(12) United States Patent
Weadock

(10) Patent No.: US 7,220,272 B2
(45) Date of Patent: May 22, 2007

(54) COMPOSITE STAPLE AND METHOD FOR USING SAME

(75) Inventor: Kevin S. Weadock, Princeton, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/463,648

(22) Filed: Jun. 17, 2003

(65) Prior Publication Data

US 2003/0216778 A1 Nov. 20, 2003

Related U.S. Application Data

(63) Continuation of application No. 09/941,008, filed on Aug. 28, 2001, now Pat. No. 6,629,988.

(51) Int. Cl.
*A61D 1/00* (2006.01)
*A61B 17/08* (2006.01)

(52) U.S. Cl. ..................................... 606/219; 606/153

(58) Field of Classification Search ........ 606/153–155, 606/219–221, 75, 151, 157, 158
See application file for complete search history.

(56) References Cited

U.S. PATENT DOCUMENTS

| | | | |
|---|---|---|---|
| 4,214,587 A * | 7/1980 | Sakura, Jr. .................. | 606/155 |
| 4,693,249 A | 9/1987 | Schenck et al. | |
| 4,747,407 A * | 5/1988 | Liu et al. ..................... | 606/153 |
| 4,887,601 A * | 12/1989 | Richards ...................... | 606/219 |
| 4,950,256 A | 8/1990 | Luther et al. | |
| 4,950,258 A * | 8/1990 | Kawai et al. ................ | 604/530 |
| 5,123,908 A | 6/1992 | Chen | |
| 5,234,447 A | 8/1993 | Kaster et al. | |
| 5,250,057 A * | 10/1993 | Chen .......................... | 606/153 |
| 5,263,973 A * | 11/1993 | Cook .......................... | 606/216 |
| 5,403,333 A | 4/1995 | Kaster et al. | |
| 5,486,187 A * | 1/1996 | Schenck ...................... | 606/153 |
| 5,662,683 A * | 9/1997 | Kay ............................ | 606/232 |
| 5,695,504 A * | 12/1997 | Gifford et al. ............... | 606/153 |
| 5,749,880 A * | 5/1998 | Banas et al. ................. | 606/198 |
| 5,755,778 A | 5/1998 | Kleshinski | |
| 5,797,933 A * | 8/1998 | Snow et al. ................. | 606/151 |
| 5,817,113 A * | 10/1998 | Gifford et al. ............... | 606/153 |
| 5,906,573 A * | 5/1999 | Aretz ............................ | 600/3 |
| 5,993,476 A * | 11/1999 | Groiso ........................ | 606/219 |
| 6,030,392 A * | 2/2000 | Dakov ......................... | 606/139 |
| 6,036,702 A | 3/2000 | Bachinski et al. | |
| 6,103,295 A * | 8/2000 | Chan et al. ..................... | 427/5 |

(Continued)

FOREIGN PATENT DOCUMENTS

WO 9962408 12/1999

*Primary Examiner*—Michael J. Hayes
*Assistant Examiner*—Michael Mendoza
(74) *Attorney, Agent, or Firm*—Nutter, McClennen & Fish LLP

(57) ABSTRACT

An anastomosis staple comprising of a plurality of vessel engaging members and a binding structure holding the vessel engaging members together is described. The binding structure has at least one bioabsorbable element. The binding structure is rigid enough to allow for deployment and quickly resorbs to avoid problems associated with intimal hyperplasia and physical hindrance of secondary interventional procedures. The vessel engaging members may be comprised of superelastic or shape memory metal and are independent from one another. The members may be equidistant from one another and embedded within the binding structure. The composite staple can preferably serve as a drug delivery vehicle.

9 Claims, 9 Drawing Sheets

U.S. PATENT DOCUMENTS

| | | | |
|---|---|---|---|
| 6,113,612 A * | 9/2000 | Swanson et al. | 623/1.15 |
| 6,322,580 B1 * | 11/2001 | Kanner | 606/213 |
| 6,348,064 B1 * | 2/2002 | Kanner | 606/219 |
| 6,352,710 B2 * | 3/2002 | Sawhney et al. | 424/426 |
| 6,364,884 B1 * | 4/2002 | Bowman et al. | 606/72 |
| 6,380,154 B1 * | 4/2002 | Cappello et al. | 514/2 |
| 6,447,524 B1 * | 9/2002 | Knodel et al. | 606/151 |
| 6,471,987 B1 * | 10/2002 | McBride-Sakal et al. | 424/447 |
| 6,666,873 B1 * | 12/2003 | Cassell | 606/153 |
| 6,932,838 B2 * | 8/2005 | Schwartz et al. | 623/1.23 |
| 2002/0055701 A1 * | 5/2002 | Fischell et al. | |

* cited by examiner

COMPOSITE STAPLE AND METHOD FOR USING SAME

CROSS-REFERENCE TO RELATED APPLICATIONS

This application is a continuation of application Ser. No. 09/941,008 filed Aug. 28, 2001 now U.S. Pat. No. 6,629,988, titled "Composite Staple For Completing An Anastomosis," which is hereby incorporated by reference in its entirety.

STATEMENT REGARDING FEDERALLY SPONSORED RESEARCH

Not applicable.

FIELD OF THE INVENTION

The present invention relates generally to medical devices for joining tubular structures. More particularly, this invention relates to anastomosis staples composed of bioabsorbable and metallic components for connecting blood vessels.

BACKGROUND OF THE INVENTION

An anastomosis is a surgical procedure by which two separate tubular bodies or ducts, usually blood vessels, are interconnected. The anastomotic connection allows body fluid to flow between the lumens of the tubular bodies without leakage at the connection site. Such a connection may be required to repair severed blood vessels. More often, anastomotic connections are utilized in order to bypass an obstruction in a patient's heart. For example, in a coronary artery bypass graft (CABG) surgery, a graft vessel is anastomosed to the coronary artery downstream from the obstruction to enable aortic blood carried by the graft vessel to be rerouted around the blockage in the coronary artery. In one case, the anastomosis may be made between the end of the graft vessel and the side wall of the coronary artery, in what is typically known as an end-to-side connection. In other instances, the anastomotic connection could be of the side-to-side type. And in certain situations, more than one anastomotic connection may be needed.

Current methods available for creating an anastomotic connection include hand suturing the vessels together. However, the use of sutures to connect interrupted vessels has inherent drawbacks. For example, suturing is difficult to perform and time-consuming, and requires great skill and experience on the part of the surgeon due in large part to the extremely small scale of the vessels. Suturing is particularly difficult in beating heart CABG surgery. Also, sutures do not always provide a fluid-tight connection at the anastomosis site. Moreover, to perform the procedure it is usually necessary to stop the heart by infusing the organ with cold cardioplegia solution. This enables a blood-free and still anastomosis site for the suturing process. However, such procedures for slowing down or stopping the heart inherently result in trauma to the organ.

Attempts have been made to provide implantable devices that connect blood vessels together in a more expedient and reliable manner. One approach is to use staples to create an anastomotic connection. For example, Kaster et al. in U.S. Pat. No. 5,234,447 describes a staple comprising a rigid metal ring having fingers radially extending therefrom. Using a staple forming tool, the fingers are deformed to urge them into engagement with the vessels' interior and exterior walls, thereby creating an anastomotic connection between the vessels.

One potential problem arising with staples having rigid annular members is compliance mismatch. The use of flexible metallic anastomotic staples for CABG procedures has recently been proposed to address this problem. Some of these flexible staples are described by Gifford, III et al. in U.S. Pat. Nos. 5,695,504 and 5,817,113, Backinski et al. in U.S. Pat. No. 6,036,702, and by Derowe et al. in WO 99/62408. These staples have flexible annular means that may reduce the rigidity of solid annular members of other staples such as the one described by Kaster et al.

In addition, use of flexible metallic stents has been contemplated to address the problem of compliance mismatch. Nevertheless, stents may eventually suffer from physiological phenomena such as intimal hyperplasia and stenosis. Gifford, III et al. in U.S. Pat. No. 5,695,504 attempts to overcome the problem of intimal hyperplasia by providing a non-absorbable flexible filament as a base to hold vessel engaging members. However, the non-absorbable flexible filament may not have the rigidity needed to deploy the staple, and may further radially constrain the vessel. Finally, the nonabsorbable filament may sterically hinder secondary interventional techniques such as balloon angioplasty that may become necessary at a future time.

Current designs for vascular anastomotic staples generally are more successful in large diameter proximal anastomoses. However, their utility in smaller diameter proximal anastomoses and distal anastomoses may be limited. Most of the anastomotic staples described in the art have rigid or substantially rigid annular members that serve as the base for vessel engaging members. These annular members may induce neointimal hyperplasia through a mechanism similar to that observed with metallic stents. Another potential problem with these annular members is that they may preclude the possibility of interventional means to address the hyperplasia, such as balloon angioplasty. Finally, rigid or semi-rigid metallic annular members may complicate the use of secondary interventional devices such as balloon or stent-carrying catheters by sterically preventing or hindering access to lesions distal to the staple.

There is thus a need for a vascular anastomosis staple that provides fast and reliable anastomosis in small diameter vessels. There is also a need for an anastomosis staple that prevents incurrence of neointimal hyperplasia. Finally, there is also a need for an anastomosis device that does not sterically hinder access to the surrounding tissue by other devices such as catheters.

SUMMARY OF THE INVENTION

The present invention avoids the aforementioned problems associated with anastomotic staples having rigid or semi-rigid annular base members by providing an anastomotic staple consisting of a plurality of vessel engaging members and a binding structure holding each of the plurality of vessel engaging members in a predefined spatial relationship. The binding structure includes at least one bioabsorbable element. As the anastomosis heals, the bioabsorbable element is resorbed, enabling at least one vessel engaging member to freely move with respect to at least one other vessel engaging member. Resorption of the bioabsorbable element relieves the anastomosis of its rigid constrainment imparted by the binding structure of the anastomosis staple.

In an exemplary embodiment, the composite staple of the present invention has a binding structure composed of a bioabsorbable polymeric or copolymeric scaffold. The scaffold is rigid enough to allow deployment of the device and quickly resorbs to avoid problems associated with intimal hyperplasia, compliance mismatch and physical hindrance of secondary interventional procedures. The scaffold may be either annular or elliptical in shape. In one aspect of this embodiment, the vessel engaging members are composed of superelastic or shape memory metal such as nitinol and are independent from one another, i.e., no metallic contacts are present from one member to the next. The members may be equidistant from one another and are embedded within the resorbable scaffold. Each vessel engaging member has a central body that is larger in diameter than the rest of the member. This central region facilitates anchorage within the bioabsorbable scaffold. In another aspect, the vessel engaging members are formed of a rigid but malleable metal such as stainless steel.

In yet another aspect of the present invention, the absorbable scaffold can act as a drug or radiation release vehicle. The scaffold may contain pharmaceutical agents and/or radioactive substances for the controlled release of such pharmaceutical agents and/or radiation after the composite staple is deployed. For example, the scaffold may contain antibiotics, anticoagulants, procoagulants, radioactive molecules with a short half-life and a β-component, such as $^{131}$I. In addition, the vessel engaging members can be coated with a radioactive substance such as $^{32}$P to reduce the likelihood of neointimal hyperplasia. The members may also be coated with a non-radioactive ligand which can be rendered radioactive with subsequent intravenous administration of radioactive ligands.

In another embodiment of the present invention, the scaffold of the composite staple has an arcuate geometry suitable for anastomosing small diameter blood vessels. The scaffold may have an arc that matches the diameter of the target vessel to which the staple is connected, enabling the staple to saddle the vessel in conformity.

In yet another embodiment of the present invention, the composite staple has a binding structure comprising a radially expandable bioabsorbable scaffold and a plurality of vessel engaging members that are at least partially embedded within the scaffold. The scaffold comprises a plurality of alternating nodes and arched bands. Embedded within each node is a vessel engaging member having at least one arm extending out of the node. Between each node is an arched band that provides radial tension to the scaffold and enables the scaffold to radially expand.

In still another embodiment of the present invention, the composite staple includes a plurality of vessel engaging members and a plurality of bridges. Each pair of adjacent vessel engaging members is connected by at least one bridge. At least one pair of adjacent vessel engaging members is connected by a bioabsorbable element. The vessel engaging members and bridges are formed of the same material. Collectively, the bridges and bioabsorbable element make up the binding structure of the composite staple. The bridges provide for radial expansion of the composite staple. The binding structure of this particular composite staple may be considered a network of elements that hold the vessel engaging members in a predefined spatial relationship and imparts enough rigidity to deploy the composite staple. Upon resorption of the bioabsorbable element of the binding structure, the anastomosis is relieved of any constrainment, enabling at least one vessel engaging member to move freely with respect to another vessel engaging member.

Finally, in yet another embodiment of the present invention, the composite staple comprises a bioabsorbable scaffold having a plurality of vessel engaging members at least partially embedded within the scaffold. The scaffold may have an annular or elliptical shape. Each of the vessel engaging members has at least one protrusion that extends beyond the outer surface of the scaffold. The protrusions provide the composite staple with a roughened surface for effecting an anastomotic connection.

Further features of the invention, its nature and various advantages, will be more apparent from the accompanying drawings and the following detailed description of the drawings and the preferred embodiments.

DETAILED DESCRIPTION OF THE DRAWINGS

Figure 1:
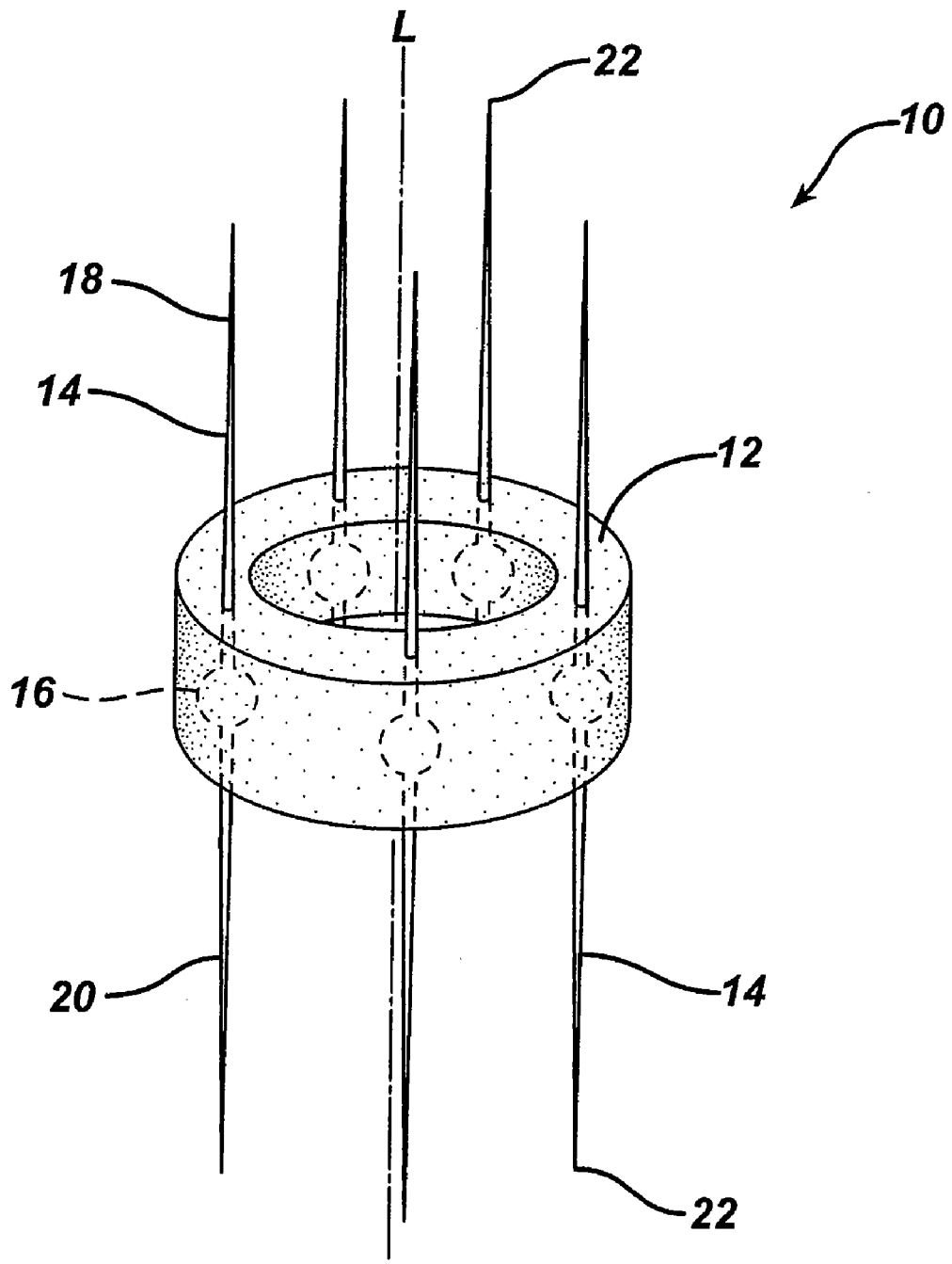
FIG. 1 is a perspective view of a composite staple of the present invention in an undeployed state.

As illustrated in FIG. 1, the composite staple 10 of the present invention includes a plurality of vessel engaging members 14 held in a predefined spatial relationship by a binding structure, shown here as scaffold 12. In an exemplary embodiment of the invention, the scaffold 12 is composed of a bioabsorbable polymer or copolymer, the polymer or copolymer being capable of resorption via hydrolysis, enzymatic degradation, or erosion. Resorption should ideally occur over a 10 to 30 day interval in vivo. The scaffold is rigid during deployment and quickly resorbs to avoid problems associated with intimal hyperplasia and physical hindrance of secondary interventional procedures. As illustrated, scaffold 12 has an annular shape; however, it is contemplated that the scaffold 12 may also be elliptical in shape.

In one embodiment, each vessel engaging member 14 includes an enlarged central body 16 that is larger in diameter than the rest of member 14. This central body 16 enables the vessel engaging member 14 to be securely anchored within the bioabsorbable scaffold 12. Extending from central body 16 is a proximal arm 18 and a distal arm 20. Proximal arm 18 and distal arm 20 are diametrically opposed. The length of each arm 18, 20 will depend on the diameter of the vessels to be joined together. The enlarged anchor portion 16 is embedded substantially within the scaffold 12, while proximal arm 18 and distal arm 20 extend away from the scaffold 12. At least one of the vessel engaging members 14 is independent from the others, i.e., metallic contacts may not be present from one member 14 to the next. As shown in FIG. 1, vessel engaging members 14 may be substantially equidistant from one another. The distance between a vessel engaging member 14 and an adjacent member may vary according to the vessels to be joined and the angle to which they are joined.

In an undeployed state, proximal arm 18 and distal arm 20 of the vessel engaging members 14 extend in an orientation such that they are substantially parallel to a longitudinal axis L of staple 10. Proximal arm 18 and distal arm 20 can extend to a hook, barb, or, as shown, sharpened point 22 for piercing through biological tissue. However, each arm 18, 20 can also extend to a blunt tip. For example, the ends of the arms 18, 20 can be shaped like paddles (not shown) that, when bent, can bear down against tissue without penetration.

Scaffold 12 can be composed of a suitable polymer or copolymer. Exemplary materials include polylactic acid-polyglycolic acid (PLA-PGA), with a predominant fraction of PGA. Other bioabsorbable polymers can be used to make the scaffold according to the present invention. Examples of suitable biocompatible, bioabsorbable polymers include polymers selected from the group consisting of aliphatic polyesters, poly(amino acids), copoly(ether-esters), poly-alkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-, L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\gamma$-valerolactone, $\beta$-butyrolactone, $\gamma$-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, $\alpha$, $\alpha$-diethylpropiolactone, ethylene carbonate, ethylene oxalate, 3-methyl-1,4-dioxane-2, 5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copolyester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208, 511; 4,141,087; 4,130,639; 4,140,678; 4,105,034; and 4,205, 399. Polyphosphazenes, co-, ter- and higher order mixed monomer based polymers made from L-lactide, D,L-lactide, lactic acid, glycolide, glycolic acid, para-dioxanone, trimethylene carbonate and $\epsilon$-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Exemplary bioabsorbable, biocompatible elastomers include but are not limited to elastomeric copolymers of $\epsilon$-caprolactone and glycolide (including polyglycolic acid) with a mole ratio of $\epsilon$-caprolactone to glycolide of from about 35:65 to about 65:35, more preferably from 45:55 to 35:65; elastomeric copolymers of $\epsilon$-caprolactone and lactide (including L-lactide, D-lactide, blends thereof, and lactic acid polymers and copolymers) where the mole ratio of $\epsilon$-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of $\epsilon$-caprolactone and p-dioxanone where the mole ratio of $\epsilon$-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof. Examples of suitable bioabsorbable elastomers are described in U.S. Pat. Nos. 4,045,418; 4,057,537 and 5,468, 253.

In one embodiment, the scaffold 12 can be used as a vehicle for the controlled release of drugs such as vasodilators or radioisotopes. The resorbable scaffold 12 may contain pharmaceutical agents and/or radioactive substances, the latter being $\beta$-type emitters such as $^{32}P$, for delayed release once the staple 10 is deployed. For example, the polymeric mixture forming the scaffold 12 can be mixed with antibiotics, anticoagulants, procoagulants, radioactive molecules with a short half-life and a $\beta$-component, such as $^{131}I$.

Vessel engaging members 14 of the present invention may be formed as unitary elements and may be composed of a variety of materials. In one embodiment, the vessel engaging members can comprise a superelastic or shape memory material. For example, the shape memory material can be a nickel alloy such as nitinol. In another embodiment, the vessel engaging members 14 can be made of a metal such as stainless steel, titanium, or titanium alloy. The vessel engaging members 14 can also be coated with a radioactive substance such as $^{32}P$ to reduce the likelihood of neointimal hyperplasia. The members 14 may also be coated with a non-radioactive ligand which can be rendered radioactive with subsequent intravenous administration of radioactive ligands.

The type of delivery system and manner of deployment utilized by the present invention depends upon what materials form the vessel engaging members 14. For nitinol-based systems, the vessel engaging members 14 will self-deploy after release from the delivery instrument. Other metal-based systems will require an anvil to flare the vessel engaging members 14. For example, in a nitinol-based system, the vessel engaging members 14 may be processed such that proximal arms 18 and distal arms 20 have specific predetermined orientations. A delivery system like the one described in U.S. Pat. No. 5,695,504 to Gifford, III et al., which is hereby incorporated by reference, can be utilized with a composite staple 10 having vessel engaging members 14 formed of shape memory material. To deploy the composite staple 10 using this system, the vessel engaging members 14 are constrained with an annular staple driver in the straightened position such as shown in FIG. 1. A graft vessel is placed within the annular staple driver and a portion of the graft vessel everted over the composite staple 10 and distal arms 20. The composite staple 10 is then pushed towards the distal end of the annular staple driver, enabling the sharpened ends 22 of the distal arms 20 to partially resume their annealed shape and pierce the everted portion of the graft vessel. Together, the annular staple driver with the composite staple 10 and attached graft vessel are then positioned at the opening to the target vessel. When the graft vessel is properly situated within the opening of the target vessel, the composite staple 10 can be completely pushed out from the annular staple driver to allow the proximal arms 18 to assume their annealed configuration. Depending on what shape the members 14 are preset to take, the proximal arms 18 can either pierce the surrounding biological tissue, or merely bear down against the target vessel to form a fluid tight seal around the opening.

For metal-based systems where the composite staple 10 includes vessel engaging members 14 formed of stainless steel or titanium, an anvil-type tool can be used to deploy the staple 10. An example of such a delivery device is described in U.S. Pat. No. 5,234,447 to Kaster et al., which is hereby incorporated by reference. In use, the composite staple 10 is mounted onto a spring-bias staple forming tool by positioning the scaffold 12 in a holding unit of the tool such that the distal arms 20 are outwardly disposed and extend beyond the distal end of the tool. A graft vessel is then displaced through a hole provided in the tool. A portion of the vessel is everted back over the composite staple 10 such that distal arms 20 pierce the blood vessel and extend therethrough. The staple forming tool can then be engaged to urge distal arms 20 into engagement with the vessel wall.

Following this, the tool may be positioned to dispose the composite staple 10 and blood vessel combination around the opening in the target vessel. The tip of the tool, including the staple 10, may be pushed through the opening, and then pulled backwards to cause the distal arms 20 engaging the graft vessel to also pierce and engage the interior wall of the target vessel. Then, by forcing a sleeve having an anvil at a distal end thereof down the shaft of the tool, the anvil will contact the proximal arms 18 and urge them into engagement with the exterior wall of the target vessel. Once the composite staple 10 is deployed, the tool may be removed.

Composite staple 10 of FIG. 1 is suitable for forming an anastomosis between a small diameter graft vessel (i.e., 3-4 mm) and a large diameter target vessel such as an aorta. Where an anastomosis is required between a small diameter graft vessel and a small diameter target vessel, i.e., one with a diameter equal to or smaller than the graft vessel, a composite staple 10' such as the one shown in FIG. 2 having an arched geometry can be used instead. Unlike a large diameter target vessel, the opening 32 on a small diameter target vessel 30 will not be substantially planar. Rather, the opening 32 is buckled due to the magnitude of curvature on a small diameter vessel.

Figure 2:
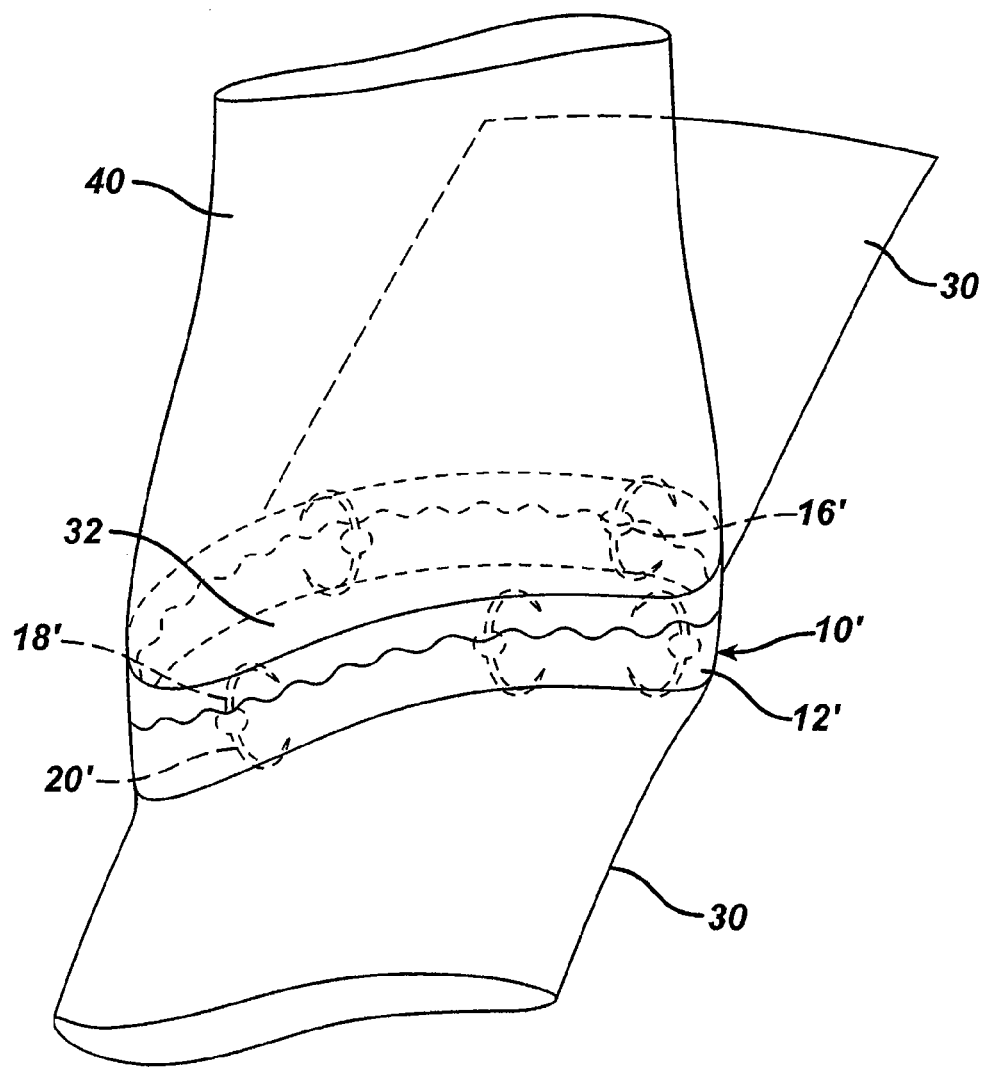
FIG. 2 illustrates another embodiment of the composite staple of the present invention in a deployed state.

To prevent undue stress and stretching of the target vessel 30 required to urge the vessel 30 into conformance with staple 10, a composite staple 10' can be provided having ascaffold 12' that follows the arc of this vessel's curvature. Scaffold 12' may be either annular or elliptical in shape. As shown in FIG. 2, the scaffold 12' of composite staple 10' may also have an arc that matches the diameter of the target vessel 30, enabling the staple 10' to saddle the opening 32 in conformity. The arched radius avoids radial stress on the wall of the target vessel 30 that might serve to flatten the vessel, resulting in a turbulent blood flow pattern. In all other respects, composite staple 10' shares the same properties and structural attributes as composite staple 10, with similar elements being denoted in the drawings with the same numeral, followed by the symbol "'".

Figure 3:
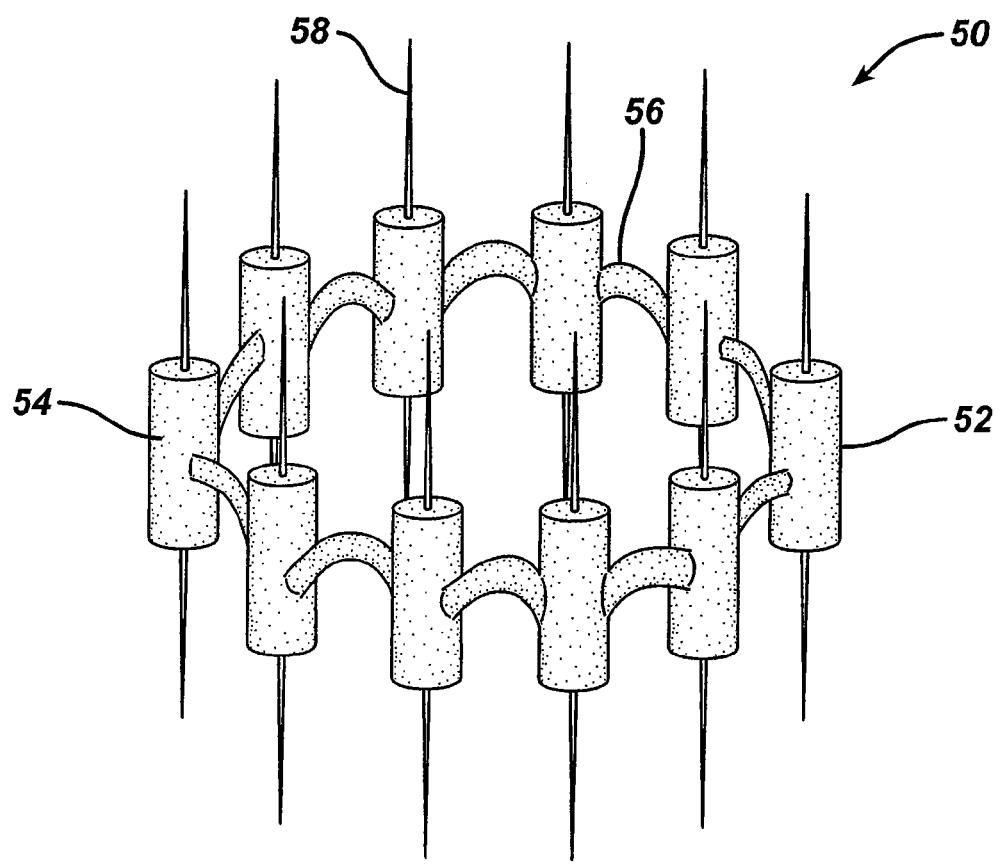
FIG. 3 is a perspective view of yet another embodiment of the present invention in an undeployed state.
Figure 4:
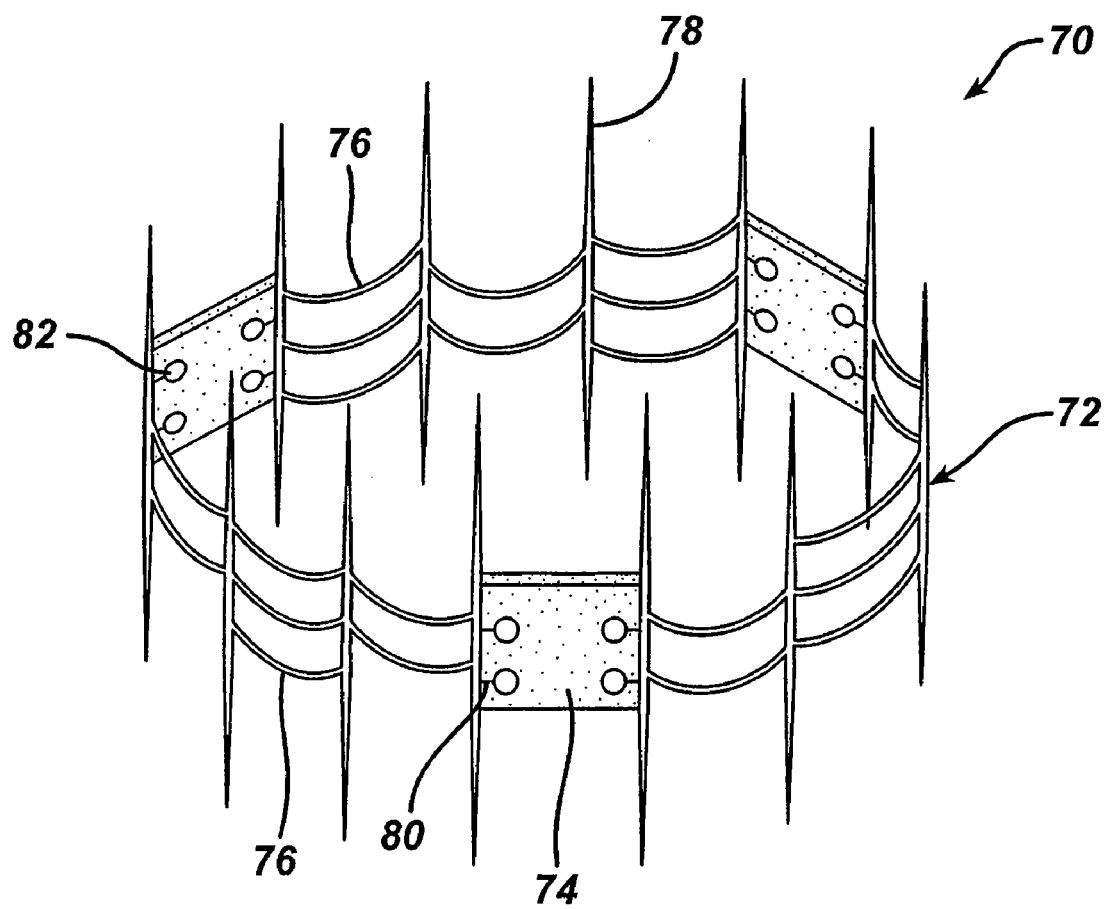
FIG. 4 is a perspective view of yet another embodiment of the present invention in an undeployed state.

The present invention also contemplates the desirability of a bioabsorbable composite staple having properties of radial expansion. FIGS. 3 and 4 illustrate various embodiments of this concept. In FIG. 3, the binding structure of composite staple 50 comprises ascaffold 52 formed of a plurality of nodes 54. Each node 54 is connected to an adjacent node 54 by an arched band 56. The scaffold 52, including the nodes 54 and bands 56, can be formed from a bioabsorbable material much like the one used for scaffold 12 shown in FIG. 1. Scaffold 52 may be either annular or elliptical in shape. Arched band may be either polymeric or formed from a metal.

Embedded within each node 54 is a vessel engaging member 58 substantially identical to the one used in composite staple 10. The vessel engaging members 58 can be insert molded into the nodes 58, which can be thickened portions of the polymeric scaffold 52. As with vessel engaging members 14, the members 58 can include an enlarged portion (not shown) for anchorage within the polymeric nodes 54. And like members 14, vessel engaging members 58 can be formed of either a superelastic or shape memory material like nitinol, or a metal such as stainless steel or titanium. As shown in FIG. 3, the arched bands 56 of composite staple 50 have a predetermined arch, or curvature, that creates radial tension and enables the scaffold 52 of staple 50 to expand.

FIG. 4 illustrates another exemplary embodiment of a bioabsorbable composite staple 70. In this embodiment, composite staple 70 comprises a plurality of vessel engaging members 78 connected to each other by a plurality of bridges 76. The number of bridges 76 between a pair of adjacent vessel engaging members 78 may vary, depending on the size and diameter of the composite staple 70. At least one pair of adjacent vessel engaging members 78 is connected by a bioabsorbable polymeric segment 74. This enables the scaffold 72 to retain its ability to break into a non-continuous annular shape, i.e., at least a C-ring formation, once the polymeric segment 74 is resorbed. It is contemplated that the number of bioabsorbable polymeric segments 74 contained in a single composite staple 70 may vary. As the anastomosis heals, the bioabsorbable segments 74 are resorbed, relieving the composite staple 70 of its rigid constrainment.

Vessel engaging members 78 may be made of superelastic or shape memory materials such as nitinol, or a metal such as stainless steel or titanium. Unlike the previously described members 14 and 58, vessel engaging members 78 of FIG. 4 do not require an enlarged portion for anchorage into polymer. Instead, vessel engaging members 78 are held in place with arched metal bridges 76. The bridges 76 may be formed of the same material as the vessel engaging members 78. These bridges 76 impart the composite staple 70 with a radial tension and the ability to flex and expand. To deploy this device, the composite staple 70 may be constrained using a sheath-like device until the staple 70 is released at the target site, whereupon the vessel engaging members 78 are activated using either the nitinol-based or metal-based systems described above. It is contemplated that the bridges 76 can be formed of a non-elastic metal such as stainless steel or titanium, in which case the composite staple 70 may be deployed using a balloon-type catheter for expanding the scaffold 72 and sealing the anastomotic site.

Collectively, the plurality of bridges 76 and the at least one bioabsorbable element 74 make up the binding structure of composite staple 70. The binding structure of this particular composite staple 70 may be considered a network of elements that hold the vessel engaging members 78 in a predefined spatial relationship and imparts enough rigidity to deploy the composite staple 70. Upon resorption of the at least one bioabsorbable element 74, the anastomosis is relieved of any constrainment, enabling at least one vessel engaging member 78 to move freely with respect to another vessel engaging member 78.

Composite staple 70 may be formed from laser cut nitinol to provide the vessel engaging members 78 and bridges 76. The polymeric segments 74 may be attached to the vessel engaging members 78 with bars 80. Bars 80 extend substantially perpendicular from vessel engaging members 78 and have an enlarged portion 82 at a distal-most end for anchorage within the polymeric segments 74.

Figure 5:
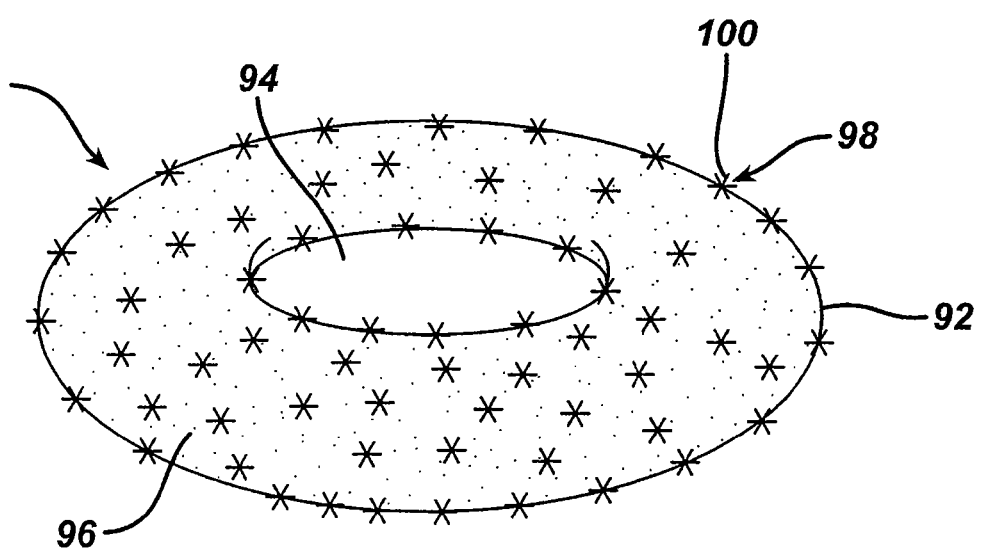
FIG. 5 is a perspective view of yet another embodiment of the present invention in an undeployed state.

In yet another embodiment of the present invention, a composite staple 90 is shown in FIG. 5. Composite staple 90 comprises a polymeric scaffold 92 shaped like a donut or lifesaver. Scaffold 92 may have either an annular or elliptical shape. The scaffold 92 may be formed of a bioabsorbable material such as those previously described. Embedded within the scaffold 92 and projecting from outer surface 96 of the scaffold 92 are vessel engaging members 98. These vessel engaging members 98 comprise spikes 100, or protrusions, that radially extend in 3-dimensions. Vessel engaging members 98 may be formed of any suitable metal such as stainless steel, titanium, or titanium alloy.

In use, opening 94 of composite staple 90 may be placed around a graft vessel. Scaffold 92 is compliant and flexible, enabling the composite staple 90 to be deployed manually or with a deployment device that urges the scaffold 92 over the end of the graft vessel (not shown). The vessel engaging members 98 surrounding the outer surface 96 of the opening 94 will enable the composite staple 90 to hold the graft vessel in place. Then, the composite staple 90 may be urged into a target vessel, the vessel engaging members 98 on the outer surface 96 piercing into the vessel walls and anchoring the composite staple 90 into the opening of the target vessel.

Figure 6:
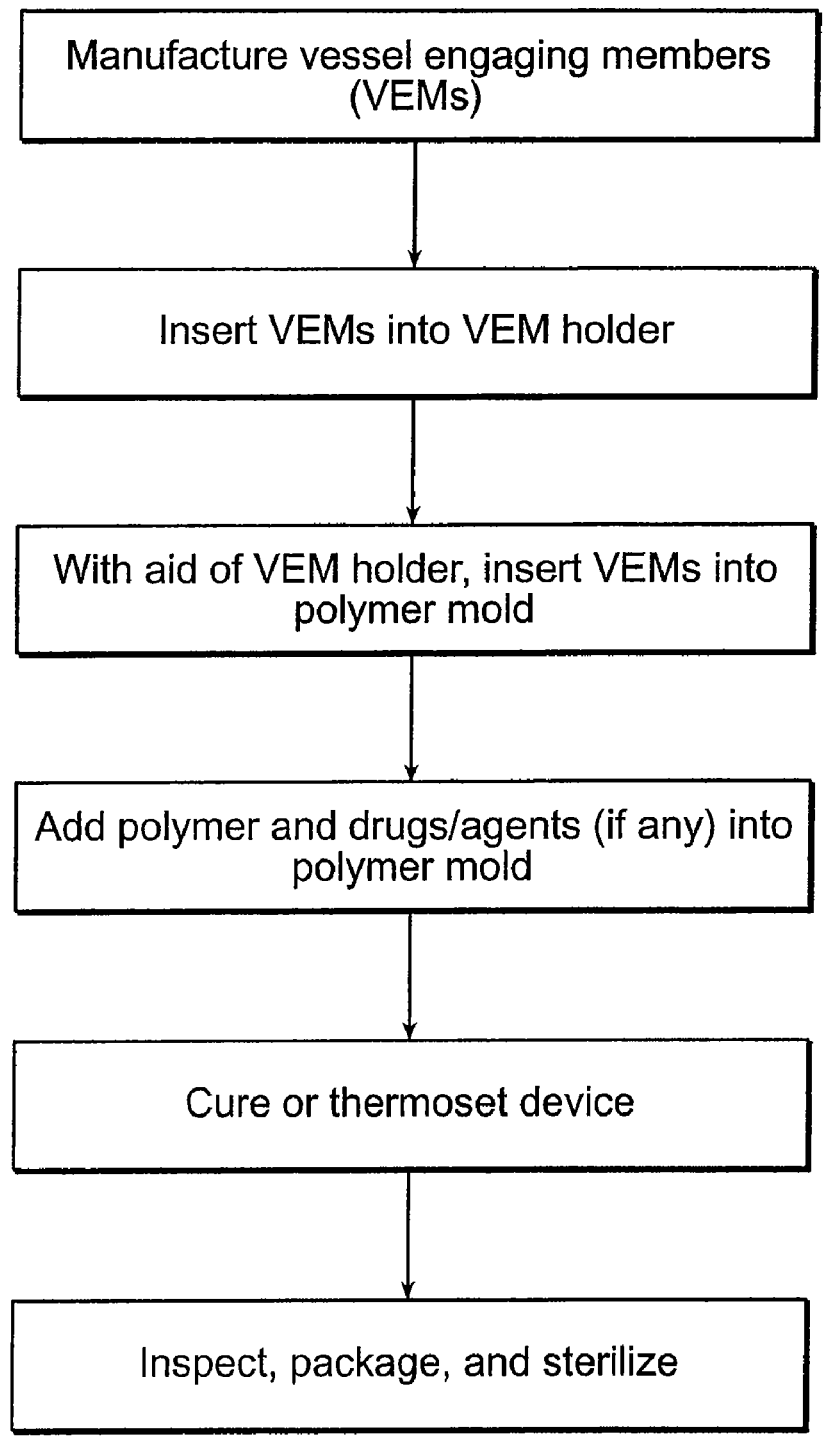
FIG. 6 is a flow chart for the manufacture of a composite staple of the present invention.

FIG. 6 represents a flowchart for the manufacture of an exemplary embodiment of the present invention. A proposed manufacturing method for making composite staple 10 would require molds for forming the annular or elliptical scaffold 12, a bioabsorbable polymer mixture and vessel engaging members 14 whose shape memory has been set. The molds would enable varying diameters of the scaffold 12, varying arching, varying thickness, etc. Within each mold would be a support or other means to hold the vessel engaging members 14 in the desired position as the polymer cures.

As shown in FIG. 6, first the vessel engaging members (VEMs) 14 are manufactured. These members 14 could comprise staples, needles, clips, etc. Once the vessel engaging members 14 are formed, the members 14 are inserted into a vessel engaging member (VEM) holder that holds the members 14 in place so that polymer can be injected around the members 14. The VEM holder may be circular or oval in shape. The number and size (i.e., length, thickness, radius of curvature) of vessel engaging members 14 can be easily varied. Pre-set members 14 can be set into the polymeric mixture at predetermined distances.

Next, the VEM holder may be inserted into a polymer mold. It is contemplated that the polymer mold may have either a circular or oval shape. In an insert molding process, the polymer mold will then receive the polymer mixture, members 14, and drugs or agents, if any. To offer controlled drug release properties, the polymeric mixture can be mixed with antibiotics, anticoagulants, procoagulants, radioactive molecules with a short half-life and β-component, such as $^{131}$I. Drugs may be delivered with the polymer, with the polymeric scaffold 12 serving as the drug reservoir. The polymer is then allowed to cure or set. Drugs sensitive to conditions during curing or setting can be inserted as small bars or balls after curing or setting. Once the polymer is set, the composite staple 10 is inspected, packaged, and sterilized.

To enhance therapeutic benefits of the composite staple 10 once deployed, the vessel engaging members 14 can also be coated with a radioactive substance such as $^{32}$P to reduce the likelihood of neointimal hyperplasia. The members 14 can also be coated with a non-radioactive ligand which can be rendered radioactive with subsequent intravenous administration of radioactive ligands.

Scaffold 12 may have an outer diameter in the range of about 1.3 to 10.0 mm, and an inner diameter in the range of about 1.0 to 7.5 mm. The wall thickness of scaffold 12 can be in the range of about 0.1 to 0.7 mm. The scaffold 12 may be in the range of about 0.8 to 10.0 mm high. Vessel engaging members 14 may have a diameter in the range of about 0.1 to 1.0 mm, with the members 14 being thicker in the center region 16. In its undeployed state, the members 14 may be in the range of about 1.0 to 5.0 mm long.

It is contemplated that the vessel engaging members 14 of the present invention can vary in length or shape (i.e., radius or curvature) to fully accommodate the target vessel anatomy. For instance, the vessel engaging members 14 may be shorter or have a smaller radius of curvature near the outside of the scaffold 12. The length of each arm 18, 20 will depend on the diameter of the vessels to be joined together. Also, vessel engaging members 14 may be manufactured with almost any desired orientation. Vessel engaging members 14 can be processed or configured upon deployment to extend either into or away from the center of the scaffold 12. Thus, composite staples of the present invention may be used for making intravascular or extravascular anastomotic connections. Finally, proximal arms 18 and distal arms 20 of vessel engaging members 14 may extend to flattened portions rather than sharpened points as shown in FIG. 1. For example, arms 18, 20 can extend into a paddle that is capable of crimping down against biological tissue without piercing the tissue.

Figure 7:
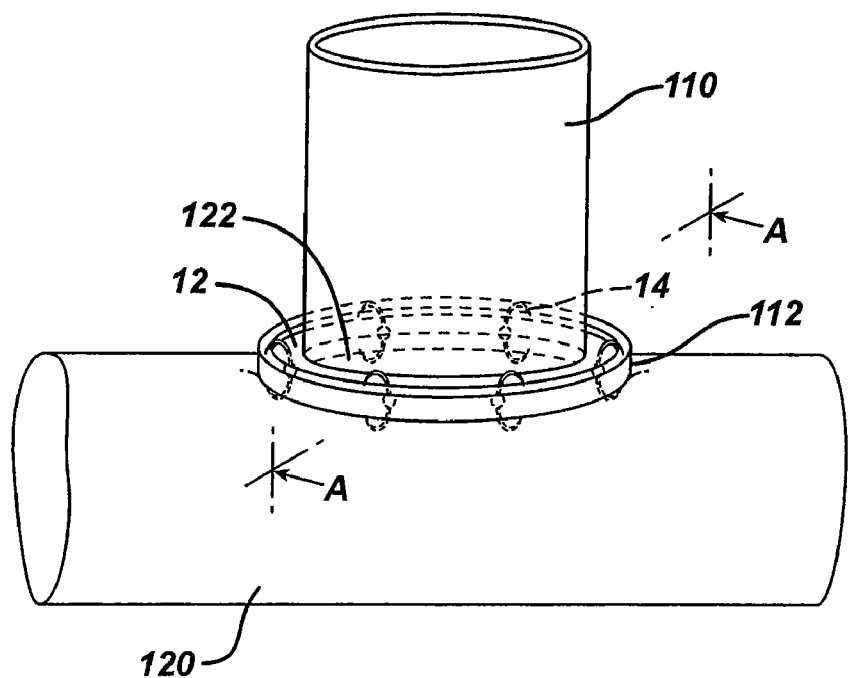
FIG. 7 illustrates the composite staple of FIG. 1 deployed in an end-to-side anastomosis.
Figure 8:
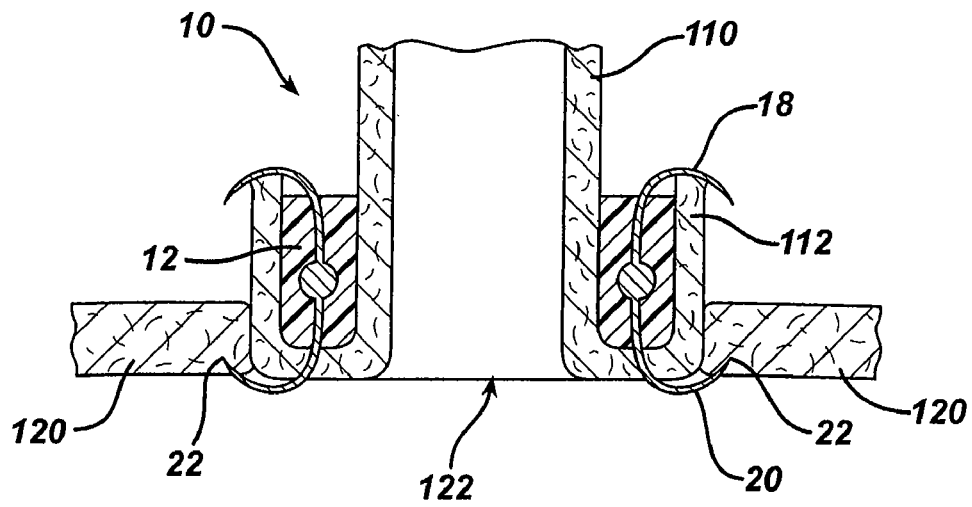
FIG. 8 is a cross-sectional view of FIG. 7 at A-A.

FIG. 7 illustrates the composite staple 10 deployed in an end-to-side anastomosis. In this exemplary method, graft vessel 110 is everted over the distal-most vessel engaging members 14. The everted graft vessel 110 is placed around the opening 122 of target vessel 120. FIG. 8 shows a cross-sectional view of the relationship between the graft vessel 110, target vessel 120, and composite staple 10. When the graft vessel 110 is in place, the distal arms 20 are then deployed so that the everted portion 112 is impaled and a connection is formed with the target vessel 120. As shown in FIG. 7, the distal arms 20 at least partially penetrate the wall of target vessel 120, the sharpened points 22 being embedded within the target vessel 120. It is preferable not to have the sharpened points 22 of distal arms 20 extend beyond the outer wall of target vessel 120. Distal arms 20 may also be configured to lie flush against the inner wall of target vessel 120 without piercing through the wall. Finally, the proximal arms 18 are then deployed to complete the anastomosis and secure the graft vessel 110 and the everted portion 112 to the target vessel. The scaffold 12 is still intact until the member 12 is completely resorbed.

Figure 9:
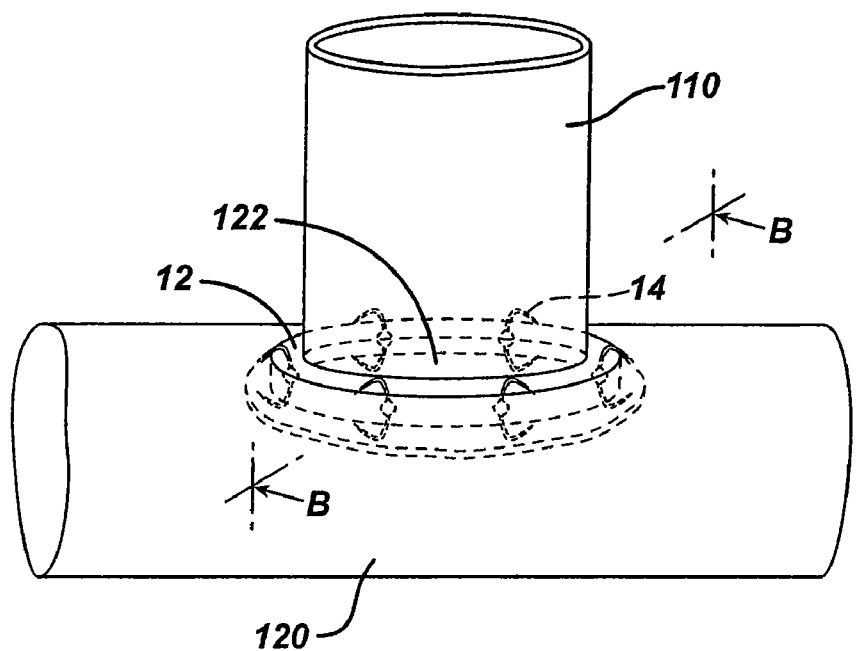
FIG. 9 illustrates the composite staple of FIG. 1 deployed in another end-to-side anastomosis.
Figure 10:
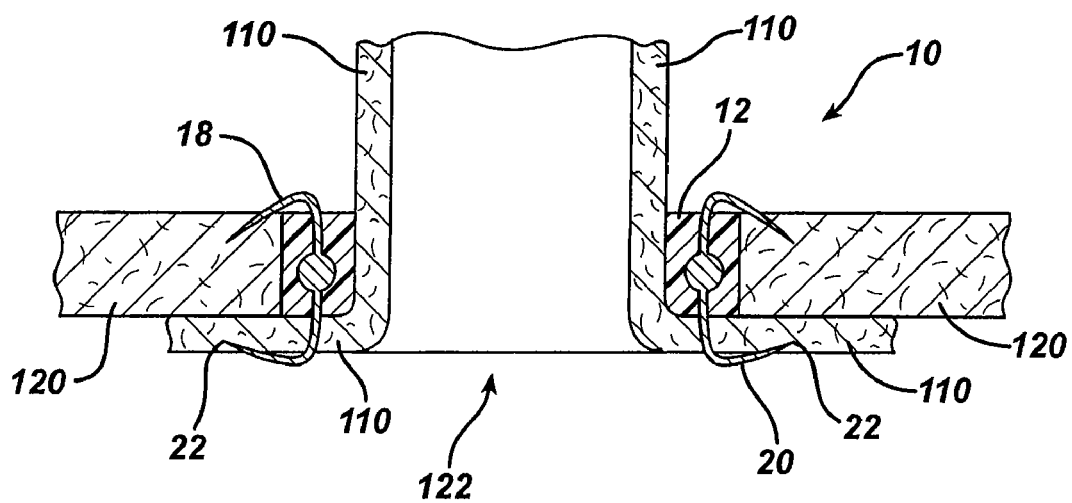
FIG. 10 is a cross-sectional view of FIG. 9 at B-B.

It is not necessary, however, that graft vessel 110 be completely everted. FIG. 9 illustrates the composite staple 10 deployed in an end-to-side anastomosis where the graft vessel 110 is only partially everted. Here, graft vessel 110 is tucked under the opening 122 of target vessel 120 in a 90° eversion, as shown in cross-section in FIG. 10. In this embodiment, distal arms 20 impale the portion of the graft vessel 110 tucked under and around the opening 122, and pierce through inner wall of target vessel 120. As shown in FIG. 9, it is preferable to have distal arms 20 partially penetrate target vessel 120. Distal arms 20 may also be configured to provide flange-like securement, lying flush against the inner wall of target vessel 120 without penetration. Proximal arms 18 may either pierce through target vessel 120 as shown, or may be preformed to lie atop the target vessel 120, crimping down against the vessel 120 without penetration (not shown). It is contemplated that graft vessel 110 may also be anastomosed to target vessel 120 without any eversion (not shown).

Figure 11A:
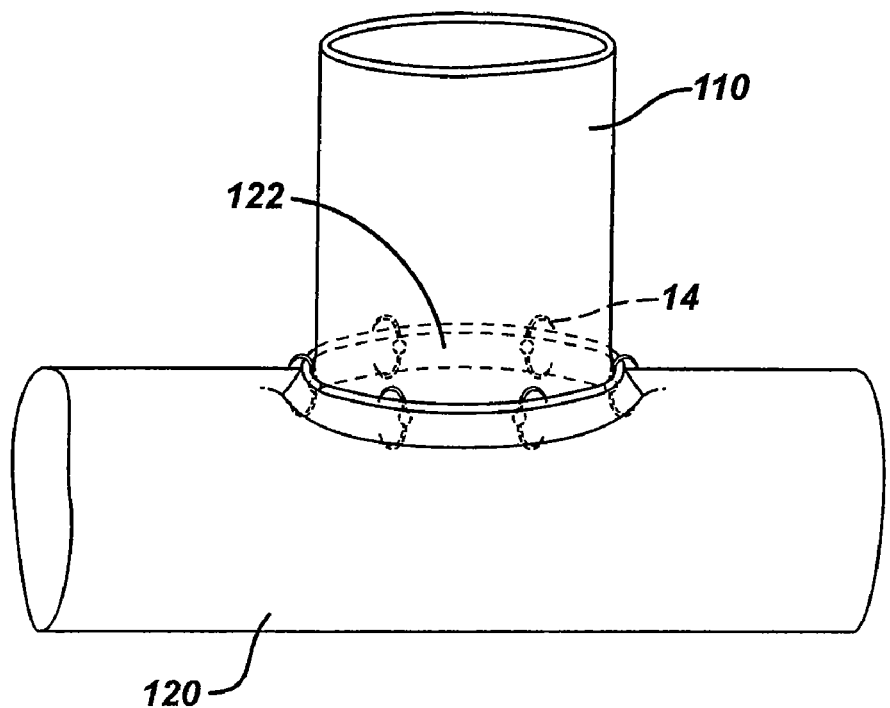
FIG. 11A shows the composite staple of FIG. 1 deployed in an end-to-side anastomosis after resorption of the bioabsorbable element.
Figure 11B:
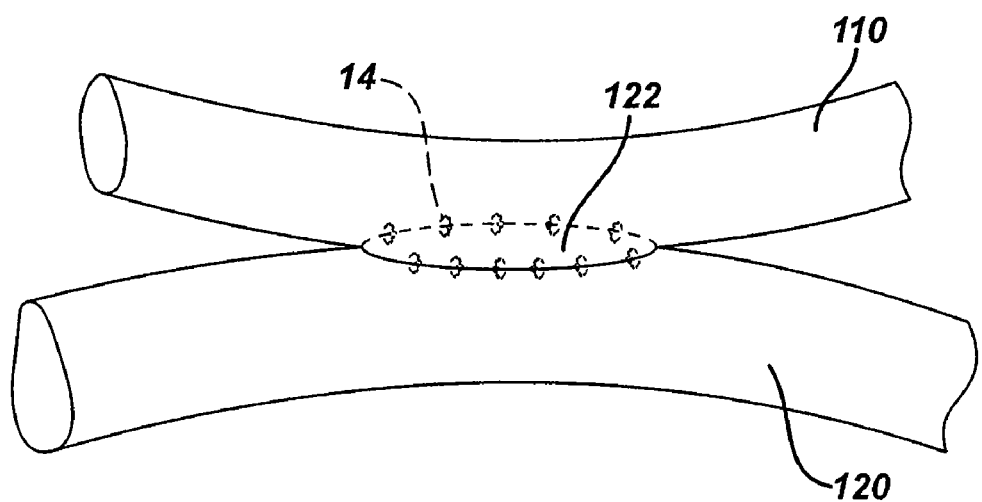
FIG. 11B shows the composite staple of FIG. 1 deployed in a side-to-side anastomosis after resorption of the bioabsorbable element.

FIG. 11A shows the composite staple 10 after the scaffold 12 has completely resorbed in an end-to-side anastomosis. FIG. 11B shows the same composite staple 10 deployed in a side-to-side anastomosis after resorption of the scaffold 12. Note that the vessel engaging members 14 still remain to provide for a secure anastomosis. By enabling the resorption of the scaffold 12, the potential for intimal hyperplasia has been reduced since the rigid scaffold 12 is no longer present. In addition, secondary interventions may proceed without the risk for hindrance or entanglement on the binding structure of composite staple 10.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A composite staple, comprising:
a binding structure having an annular shape with an outer surface surrounding a central opening, the binding structure being formed of a bioabsorbable material; and
a plurality of vessel engaging members embedded in the outer surface of the binding structure, each vessel engaging member comprising a plurality of protrusions that extend radially in three dimensions,
wherein the binding structure includes at least one bioabsorbable element configured such that at least one of the plurality of vessel engaging members is free to move with respect to at least one other of the plurality of vessel engaging members after the bioabsorbable element has resorbed.

2. The composite staple of claim 1, wherein the outer surface of the binding structure has a shape selected from the group consisting of a circle and an ellipse.

3. The composite staple of claim 1, wherein the binding structure is a bioabsorbable scaffold.

4. The composite staple of claim 3, wherein the bioabsorbable scaffold is formed from a mixture of polylactic acid and polyglycolic acid.

5. The composite staple of claim 3, wherein the bioabsorbable scaffold contains pharmaceutical or radioactive substances.

6. The composite staple of claim 5, wherein the pharmaceutical or radioactive substances are selected from the group consisting of antibiotics, anticoagulants, procoagulants, and radioisotopes with a β-component.

7. The composite staple of claim 6, wherein the radioisotopes are $^{32}$P and $^{131}$I.

8. The composite staple of claim 1, wherein at least one of the plurality of vessel engaging members are coated with a radioactive substance.

9. The composite staple of claim 8, wherein the radioactive substance is $^{32}$P or $^{131}$I.

* * * * *